United States Patent [19]

Van Iten

[11] Patent Number: 5,154,715
[45] Date of Patent: Oct. 13, 1992

[54] ABSORBENT ARTICLE HAVING A CLASP AND A METHOD OF FASTENING THE ABSORBENT ARTICLE TO AN ADJACENT GARMENT

[75] Inventor: Thomas P. Van Iten, Neenah, Wis.

[73] Assignee: Kimberly-Clark Corporation, Neenah, Wis.

[21] Appl. No.: 737,571

[22] Filed: Jul. 26, 1991

Related U.S. Application Data

[63] Continuation of Ser. No. 492,023, Mar. 12, 1990, abandoned.

[51] Int. Cl.$^5$ .................. A61F 13/15; A61F 13/20
[52] U.S. Cl. .................. 604/387; 604/385.1; 604/386; 604/389
[58] Field of Search ............ 604/386, 387, 385.1, 604/389; 24/304

[56] References Cited

U.S. PATENT DOCUMENTS

| | | | |
|---|---|---|---|
| 2,890,701 | 6/1959 | Weinman | 128/291 |
| 2,949,114 | 8/1960 | De Woskin | 128/290 |
| 3,315,677 | 4/1967 | Tyrrell, Jr. | 604/387 |
| 3,420,236 | 1/1969 | De Woskin | 128/291 |
| 3,460,535 | 8/1969 | Behna | 128/288 |
| 3,704,710 | 12/1972 | Fifer | 128/288 |
| 3,749,095 | 7/1973 | Toyama | 128/288 |
| 4,285,343 | 8/1981 | McNair | 128/287 |
| 4,589,876 | 5/1986 | Van Tilburg | 604/385 |
| 4,608,047 | 8/1986 | Mattingly | 604/387 |
| 4,609,373 | 9/1986 | Johnson | 604/389 |
| 4,687,478 | 8/1987 | Van Tilburg | 604/387 |
| 4,701,178 | 10/1987 | Glaug et al. | 604/387 |
| 4,759,754 | 7/1988 | Korpman | 604/387 |
| 4,846,828 | 7/1989 | Mendelson | 604/387 |
| 4,900,320 | 2/1990 | McCoy | 604/389 |
| 4,911,701 | 3/1990 | Mavinkurve | 604/386 |
| 4,917,697 | 4/1990 | Osborn, III et al. | 604/387 |
| 4,936,839 | 6/1990 | Molee et al. | 604/385.1 |
| 4,950,264 | 8/1990 | Osborn, III | 604/385.1 |
| 5,087,254 | 2/1992 | Davis et al. | 604/386 |
| 5,098,422 | 3/1992 | Davis et al. | 604/385.1 |

FOREIGN PATENT DOCUMENTS

| | | | |
|---|---|---|---|
| 0337438 | 10/1989 | European Pat. Off. | 604/387 |
| 0464854A1 | 7/1991 | European Pat. Off. | |
| 0862763 | 3/1961 | United Kingdom. | |

Primary Examiner—David Isabella
Assistant Examiner—A. P. Zuttarelli
Attorney, Agent, or Firm—Thomas J. Connelly

[57] ABSTRACT

An absorbent article having a clasp and a method of fastening the absorbent article to an adjacent garment is disclosed. The absorbent article includes a first member and clasp means for holding the first member secure to an adjacent garment, such as to the crotch portion of an undergarment. The clasp means includes two relatively stiff portions joined together by a hinge which permits bending of one portion relative to the other portion. At least one of the portions has an arcuate shape along the length thereof and extends outward from the first member. The arcuate portion is designed to pivot on the hinge and forcefully press the undergarment towards the first member when the absorbent article is worn.

12 Claims, 5 Drawing Sheets

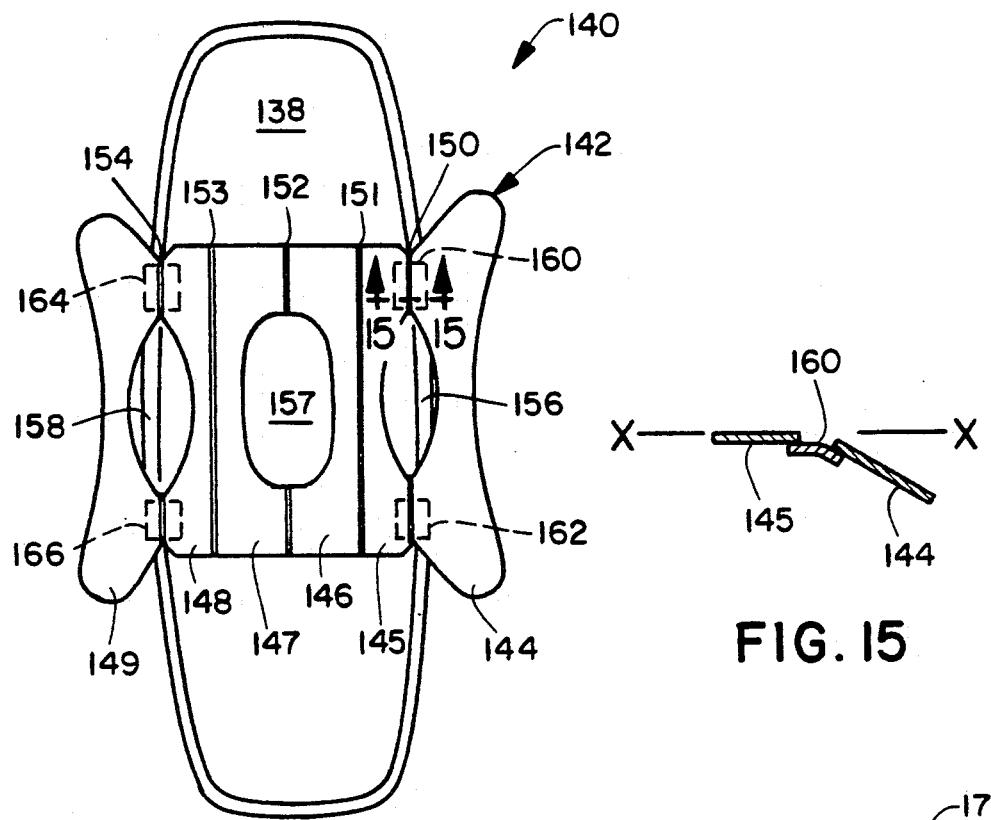
FIG. 14
FIG. 15
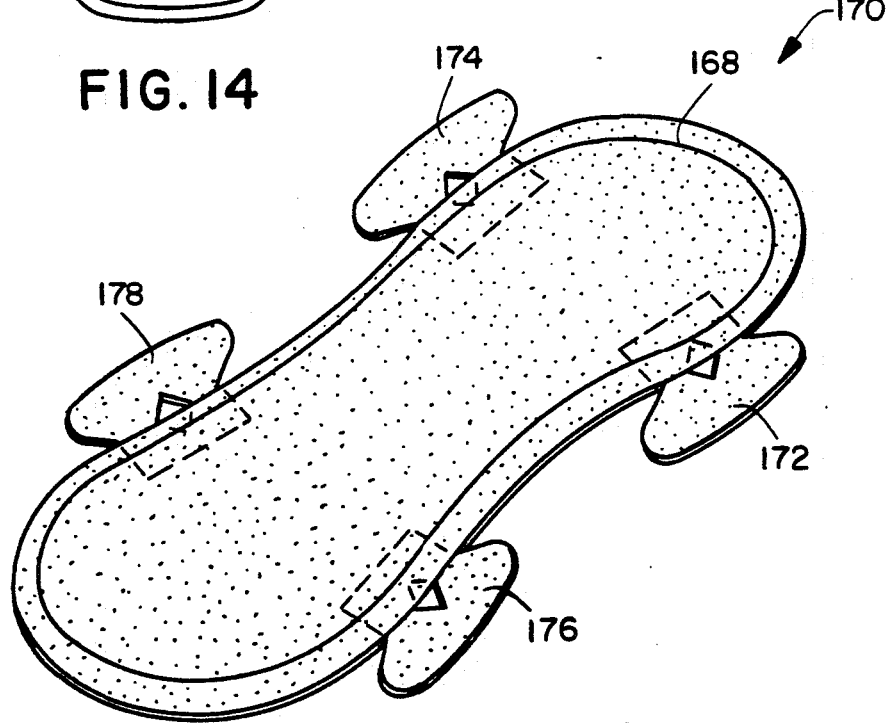
FIG. 16

ABSORBENT ARTICLE HAVING A CLASP AND A METHOD OF FASTENING THE ABSORBENT ARTICLE TO AN ADJACENT GARMENT

This is a continuation of copending application Ser. No. 07/492,023 filed on Mar. 12, 1990, abandoned.

FIELD OF THE INVENTION

This invention relates to an absorbent article having a clasp and a method of fastening the absorbent article to an adjacent garment.

BACKGROUND OF THE INVENTION

Generally, absorbent articles like sanitary napkins, overnight pads, pantiliners, incontinent garments and even some underarm shields are designed to be attached to an adjacent garment, such as an undergarment, in order to hold the product stationary during use. Pressure sensitive adhesives provide one method currently employed to affix a product to an adjacent garment. The pressure sensitive adhesive is normally applied to the undergarment facing surface of the product and is temporarily covered by a releasable peel strip. Although adhesive is widely used today, it does exhibit some disadvantages. First, the cost of the adhesive and the releasable peel strip will increase the overall cost of the product. Second, during manufacture special equipment and extra steps are required to apply the adhesive to the absorbent article and then center the peel strip over the adhesive. Third, the adhesive can be a nuisance in that it tends to stick to the inner surface of an undergarment and can leave a tacky residue once the absorbent article is removed. The build up of this residue will stain and can eventually ruin the undergarment. Fourth, it is difficult to reposition the absorbent article in the undergarment once the adhesive has been attached to the undergarment. Representative samples of adhesive attachments can be found in U.S. Pat. Nos. 4,687,478; 4,701,178 and 3,315,677.

Still, other means for holding an absorbent article secure to an undergarment includes mechanical type fasteners. These include buttons, button holes, hooks and loops, end extensions and tabs which are designed to interlock or engage some type of supporting belt or strap. These types of fasteners are being used less frequently today because they are difficult to attach and some are not very discrete under tight fitting clothing. Representative samples can be found in U.S. Pat. Nos. 4,609,373; 3,749,095; 3,704,710; 3,460,535; 3,420,236; 2,949,114; 2,890,701 and British patent 862,763.

Another approach to holding an absorbent article in place during use is to utilize attachments built into the product which function in combination with the undergarment. Representative structures include side flaps and wings which partially or completely wrap around the crotch portion of an undergarment. Some, like European patent application 0,337,438 appear to only prevent sideways movement, while others, like U.S. Pat. Nos. 4,285,343; 4,589,876; 4,608,047 and 4,759,754 utilize flaps which wrap completely around the crotch portion of an undergarment and are held together by tape or adhesive. Many of these types of fasteners are cumbersome to apply or require extra material to form the flaps.

Now an absorbent article having a clasp has been developed, along with a method of fastening the absorbent article to an undergarment. The clasp is relatively stiff and can bend about a hinge line so as to prevent sideways and lengthwise movement of the absorbent article relative to an undergarment.

SUMMARY OF THE INVENTION

Briefly, the present invention relates to an absorbent article having a first member and a clasp for holding the first member secure to an adjacent garment. The clasp includes at least two portions joined together by a hinge which permits bending of one portion relative to the other portion. At least one of the portions has an arcuate shape along the length thereof and extends from the first member. The arcuate portion is designed to pivot on the hinge and forcefully press the garment towards the first member when the absorbent article is worn.

The method of fastening the absorbent article to an adjacent garment is also disclosed. The method includes positioning the absorbent article onto the interior surface of a garment with the arcuate portion extending outward therefrom. The arcuate portion is then folded about the hinge and around a portion of the garment. The arcuate portion presses the garment against the absorbent article when a downward force is applied approximately at the upper surface of the clasp. For a sanitary napkin, the downward force is supplied when the human body contacts the sanitary napkin as the undergarment is pulled up around the torso of the person. The applied force will vary depending upon the size and weight of the user and the type of undergarment being worn.

The general object of this invention is to provide an absorbent article with a clasp which will securely hold the absorbent article against an adjacent garment. A more specific object of this invention is to provide an absorbent article with a stiff clasp which can bend about a hinge line and hold the absorbent article stationary relative to an undergarment.

Another object of this invention is to provide a quick and easy method of fastening an absorbent article to an undergarment.

Still, another object of this invention is to provide an absorbent article having one or more clasps which will prevent sideways as well as lengthwise movement of the absorbent article in the crotch portion of an undergarment.

Still further, an object of this invention is to provide an absorbent article which does not require adhesives nor costly peel strips to hold the absorbent article stationary in the crotch portion of an undergarment.

Still further, another object of this invention is to provide a cheaper absorbent article which will maintain it's position relative to an adjacent undergarment.

Other objects and advantages of the present invention will become apparent to those skilled in the art in view of the following description and the accompanying drawings.

BRIEF DESCRIPTION OF THE DRAWINGS

FIG. 14 is a bottom view of an absorbent article, such as a sanitary napkin, having a clasp with multiple portions joined by several hinges.

FIG. 15 is an enlarged, partial cross-sectional view of an elastic hinge member shown in FIG. 14 and taken along line 15—15.

FIG. 16 is a perspective view of an absorbent article having four separate clasps.

DETAILED DESCRIPTION OF THE PREFERRED EMBODIMENTS

Figure 1:
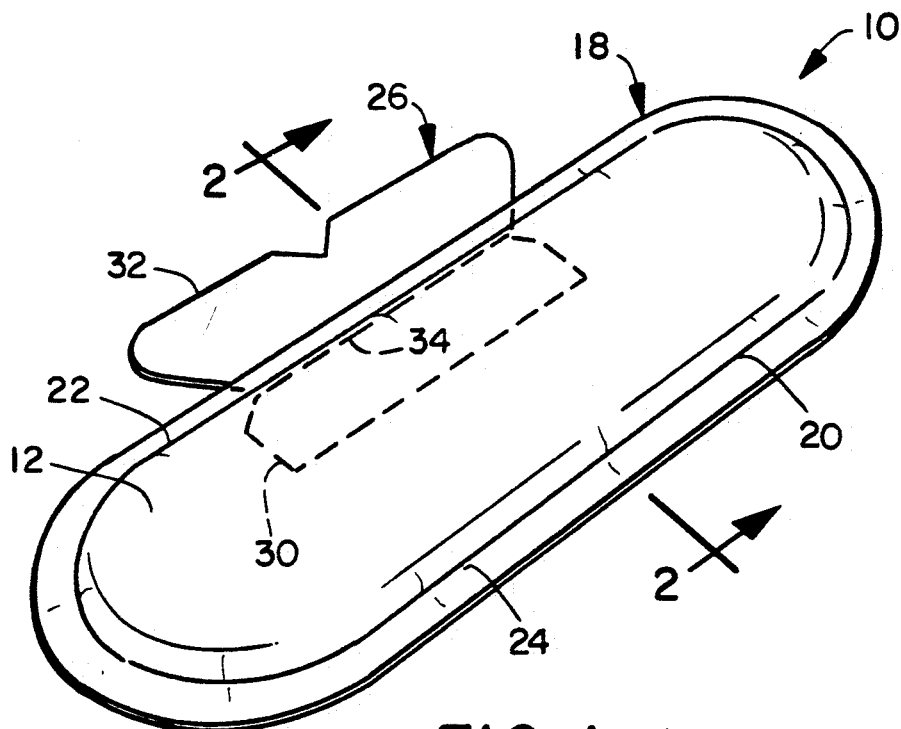
FIG. 1 is a perspective top view of an absorbent article, such as a sanitary napkin, having a single clasp attached to the bottom of the article for securing the article to an adjacent garment.
Figure 2:
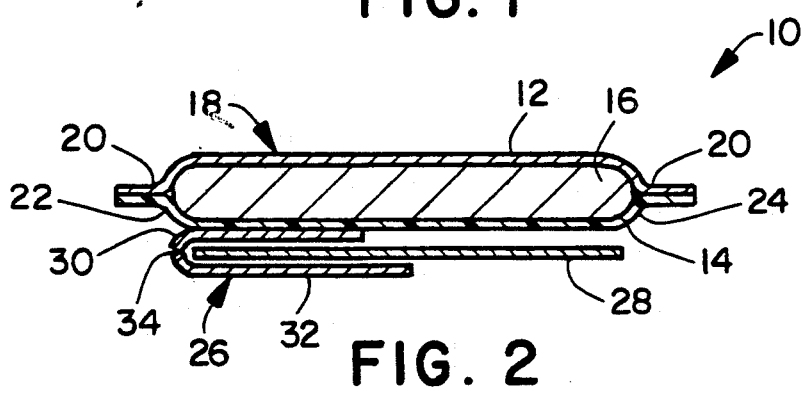
FIG. 2 is a cross-sectional view of the absorbent article shown in FIG. 1 taken along line 2—2, except the clasp has been pivoted about the hinge into a locking position with an adjacent garment.

Referring to FIGS. 1 and 2, an absorbent article 10, such as a sanitary napkin, pantiliner, incontinent garment, urinary shield, or underarm pad is shown. For purposes of discussion only, the absorbent article 10 will be described as a feminine pad or sanitary napkin. The absorbent article 10 is depicted as having a liquid permeable cover 12, a liquid-impermeable baffle 14, and an absorbent 16 positioned therebetween which forms a pad 18. The cover 12, which is designed to contact the wearer's body, can be made from a woven or nonwoven, natural or synthetic material which is easily penetrated by body fluids. Thermoplastic polymer films made from fibers or filaments of polyethylene or polypropylene are preferred. It is also beneficial to aperture the cover 12 to increase the rate at which the body fluids can penetrate down into the absorbent 16.

The baffle 14 faces the inner surface of an undergarment and is usually designed to permit the passage of air and moisture vapor to the outer surface while blocking the passage of fluids or liquids. The baffle 14 can be made from a polymeric film such as polyethylene, polypropylene or cellophane, or be made from a bicomponent film. A preferred material is ethyl-vinyl-acetate/polyethylene coextruded film. The baffle 14 can also be constructed from a liquid permeable material that has been treated or coated to become liquid-impervious. The absorbent 16 is hydrophilic and can be made from cellulose fibers, wood pulp, regenerated cellulose or cotton fibers, or a blend of pulp and other fibers. The absorbent 16 is usually resilient for enabling the pad 18 to bend easily without excessive distortion. Hydrocolloidal material, commonly referred to as superabsorbents, can also be added to the hydrophilic material to increase the absorption capacity.

The cover 12 and the baffle 14 can be attached or Joined together, such as by a peripheral seal 20, to enclose the absorbent 16. It should be noted that the cover 12 can be wrapped entirely about the absorbent 16 and then the baffle 14 can be attached to the lower surface of the cover 12 by end seals, not shown. The feminine pad 18 has longitudinally extending sides 22 and 24 and usually has an overall length of between about 6 to 12 inches and a width of between about 2 to 3.5 inches. The thickness of the pad 18 can vary from a couple of millimeters to about an inch. The absorbent article 10 further has clasp means 26 which enables the pad 18 to be fastened ad secured to an adjacent garment, preferable to the crotch portion of an undergarment 28. The clasp means or clasp 26 can consist of one or more relatively stiff members each having at least two portions 30 and 32 joined together by a hinge 34. The hinge 34 can be an axis of flexibility such as a flexible line. The hinge 34 can be a straight line, a curved line or be formed from two or more intersecting lines. The hinge 34 can be a "permanent hinge" or a "living hinge" which will permit one portion to pivot or bend relative to the other portion. A "living hinge" is known in the plastic art to be a hinge formed of a thermoplastic material which has a reduced cross-sectional thickness and can flex a certain number of times before it fails.

The second portion 32 of the clasp 26 can be initially formed parallel to the first portion 30 or be angularly disposed thereto. The clasp 26 can be integrally formed with the pad 18, or it can be attached to an exterior surface, for example to the baffle 14, by an adhesive. In FIGS. 1 and 2, the clasp 26 is shown having the first portion 30 permanently attached to the exterior surface of the baffle 14.

The clasp 26 should be bendable and can be made out of a stretchable or elasticized plastic material such as a thermoplastic film. A preferred material is polyethylene. Other resilient materials include those used as collar stiffeners or as backing material used in the garment industry. Preferably, the clasp 26 will be stiffer and more rigid than the remaining portions of the pad 18 and will be thicker than the baffle 14. The clasp 26 should not be so flimsy so as mitigate the purpose of the hinge 34. The clasp 26 should be sufficiently resilient to be comfortable yet stiff enough to provide a clasping force against the undergarment 28. An example of a comparable stiffness would be a piece of thin cardboard. The material should be heat and/or pressure formable so that it can be preformed into a desired shape such as by molding. Preferably, the material will be capable of retaining a given shape or configuration once it is molded.

Figure 3:
FIG. 3 is a schematic cross-sectional view of a clasp showing a single layer of material.
Figure 4:
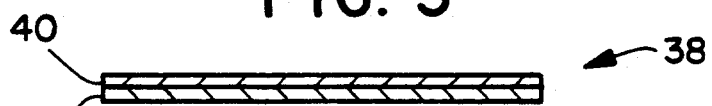
FIG. 4 is a schematic cross-sectional view of a clasp formed as a two layer laminate.
Figure 5:
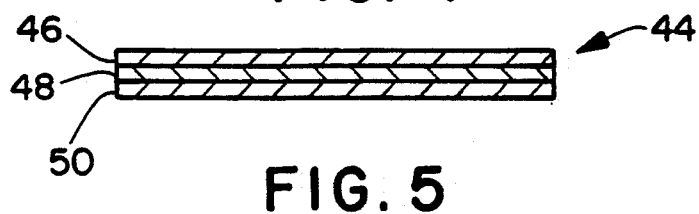
FIG. 5 is a schematic cross-sectional view of a clasp formed as a three layer laminate.

Referring to FIGS. 3, 4 and 5, the clasp 26 can be formed from a single layer of material 36, or it can be a laminate. In FIG. 4, a two layer laminate 38 is depicted containing a liquid permeable upper layer 40 and a liquid-impermeable lower layer 42. In FIG. 5, a three layer laminate 44 is depicted containing a liquid permeable upper layer 46, an absorbent layer 48 and a liquid-impermeable lower layer 50. It should be noted that it is possible to form one or more layers of the clasp 26 integral with the cover 12, the baffle 14 and the absorbent 16 if desired. The clasp 26 can have a thickness of between about 0.001 to 0.125 inches, and preferably, between about 0.05 and 0.07 inches.

The second portion 32 of the clasp 26 has an arcuate shape along the length thereof which functions to press and squeeze the undergarment 28 towards and against the first portion 30 when in a closed position. The clasp 26 is designed to squeeze tighter when the pad 18 is worn. This happens because when the pad 18 is worn it will acquire or mold to the shape of the body and this contouring causes a force to impinge on the clasp. This downward force causes the hinge 34 to bend which in turn causes the second portion 32 to press against the first portion 30.

Referring again to FIG. 2, the second portion 32 is in a "closed position" when it is pivoted on the hinge line 34 to an angle of less than 20° relative to the first portion 30. Preferably, the angle is between about 0° and 5°.

Once the absorbent article 10 has been positioned in the crotch portion of an undergarment 28, the wearer simply folds the second portion 32 about the hinge 34 to the closed position thereby trapping the undergarment therebetween. The woman will then pull the undergarment 28 up about her torso and the pad 18 will contact and conform to her body. The body forces exerted on the pad 18 will cause the hinge line 34 to bend and this causes the second portion 32 to forcefully press against both the undergarment 28 and against the first portion 30. This action causes the clasp 26 to tightly grip and hold the pad 18 stationary to the undergarment 28. The woman's weight, when she sits or moves, also creates additional forces which assist in biasing the second portion 32 against the first portion 30 and presses the undergarment 28 therebetween.

The second portion 32 can be preformed so as to have an arcuate shape before assembly or it can be configured after assembly with the pad 18. One way to shape the second portion 32 beforehand is to mold the clasp 26 out of a thermoplastic material. The material is placed in a mold and elevated to a temperature above its plasticizing point. The material is then cooled to room temperature wherein it acquires a permanent set. This permanent set can also be described as acquiring a memory. The arcuate shape is obtained by forming an arc in the mold having a radius of about 5 to 9 inches, preferably a radius of about 5.5 to 8.5 inches, and most preferably a radius of about 7 to 8 inches. The second portion 32 can also contain an arcuate shape across its width if desired. The degree of arc is preferably at least as great as the arc of the pad 18 when worn against the body.

Figure 6:
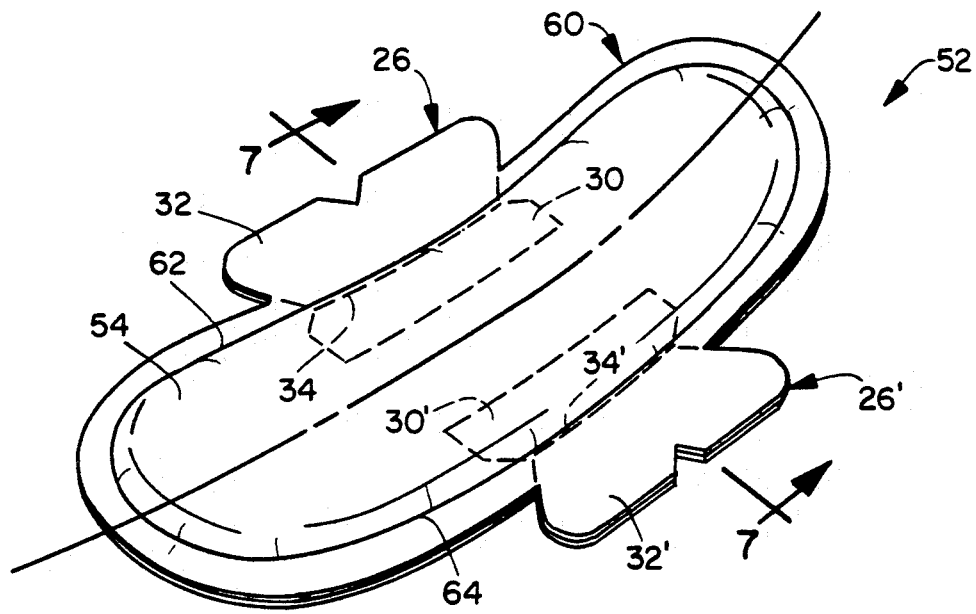
FIG. 6 is a perspective top view of an absorbent article having a pair of clasps integrally formed with the article which extend outward from each longitudinal side.
Figure 7:
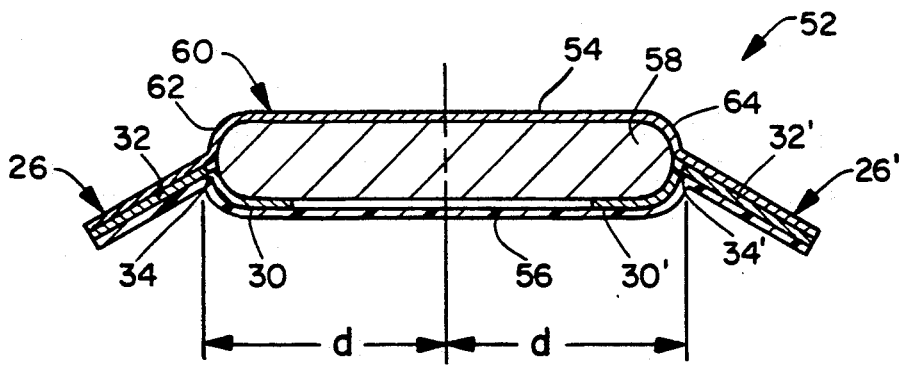
FIG. 7 is a cross-sectional view of the absorbent article shown in FIG. 6 taken along line 7—7.

Referring to FIGS. 6 and 7, an absorbent article 52 is shown having a liquid permeable cover 54 and a liquid-impermeable baffle 56 which cooperate to enclose an absorbent 58 and form a feminine pad 60. The pad 60 has a pair of longitudinally extending sides 62 and 64 from which extend clasps 26 and 26'. The clasps 26 and 26' are identical in appearance but are arranged in a mirror-like relationship to the longitudinal centerline of the pad 60. The clasps 26 and 26' can have a length of between about 1 to 6 inches, preferably about 2.5 to 4.5 inches. The width can be relatively narrow when compared to the width of the pad 60. For example, the width can be between about 0.5 to 2.5 inches and preferably about 0.75 inches. It should be noted that the dimensions of the clasps 26 and 26' can vary depending upon the size of the absorbent article itself. Furthermore, when only one clasp 26 is present, it will usually be larger in size than when two or more clasps are utilized.

As can be seen in FIG. 7, the clasps 26 and 26' are integrally formed with the pad 60 and are positioned between an extension of the cover 54 and the baffle 56. The first portions 30 and 30' are located within the pad 60 between the baffle 56 and the absorbent 58. The second portions 32 and 32' extend outward from the longitudinal sides 62 and 64. The hinges 34 and 34' join the first and second portions 30 and 30', and 32 and 32' together. The hinges 34 and 34' could be located at the longitudinal centerline of the pad 60 but preferably are located away from the longitudinal centerline and may extend beyond the outside edges 62 and 64. Preferably, the hinges 34 and 34' are situated a distance (d) of between about 0.5 and 1.5 inches from the longitudinal centerline of the pad 60.

The second portions 32 and 32' are arcuately formed and have a convex shape relative to the upper surface of the cover 54 when in an initial outwardly extending position. The second portions 32 and 32' are stiff compared to the pad 60 and are capable of pivoting or swinging around the hinges 34 and 34' to a closed position wherein they are arranged concave to the upper surface of the cover 54. When the second portions 32 and 32' are folded adjacent to the first portions 30 and 30', they can overlap between 20 to 80% of the exterior surface of the baffle 56. The exact amount will depend on the size of the clasps 26 and 26' as well as on the size of the pad 60.

Figure 8:
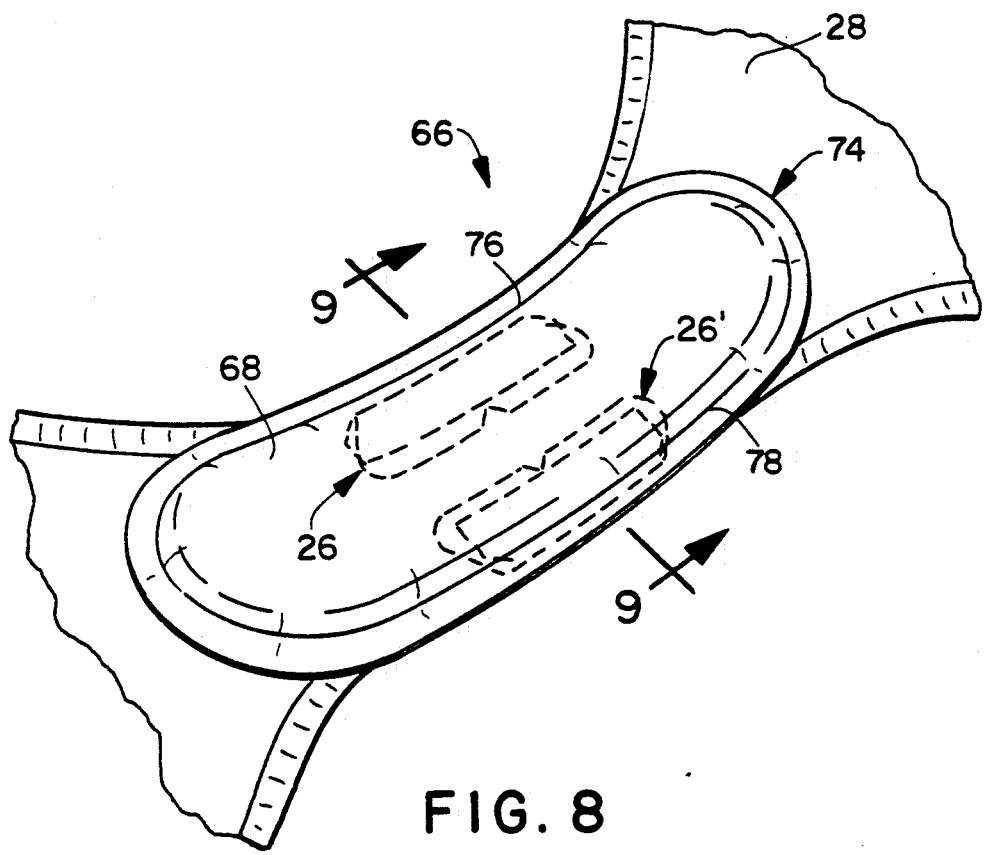
FIG. 8 is a perspective view of an absorbent article securely attached to an undergarment by a pair of clasps.
Figure 9:
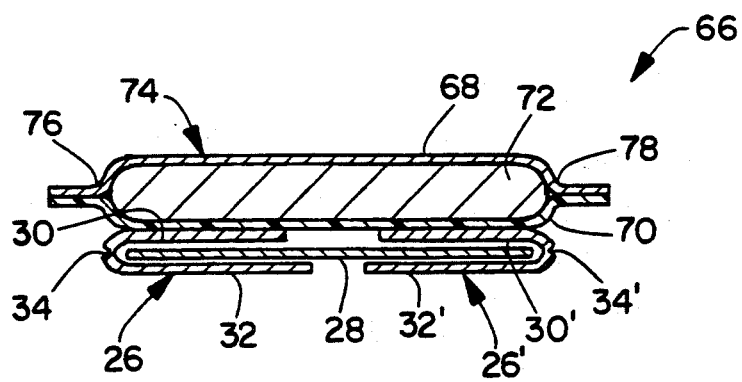
FIG. 9 is a cross-sectional view of the absorbent article and undergarment shown in FIG. 8 taken along line 9—9.

Referring to FIGS. 8 and 9, an absorbent article 66 is shown securely fastened to the crotch portion of the undergarment 28. The absorbent article 66 has a liquid permeable cover 68 and a liquid-impermeable baffle 70 which cooperate to enclose an absorbent 72 and form a feminine pad 74. The pad 74 has a pair of longitudinally extending sides 76 and 78 from which extend clasps 26 and 26'. The clasps 26 and 26' are identical in appearance and each has a first portion 30 and 30' and a second portion 32 and 32' joined by a hinge 34 and 34'. FIGS. 8 and 9 differ from FIGS. 6 and 7 in that the clasps 26 and 26' are attached to the lower surface of the baffle 70. However, as shown in FIGS. 6 and 7, the two clasps 26 and 26' provide two separate areas where the undergarment 28 is gripped and squeezed between the first portions 30 and 30' and the second portions 32 and 32'. The clasps 26 and 26' create self-holding members which are capable of exerting a pressure onto the two areas of the undergarment 28 as a bending force is applied to the upper surface of the clasps 26 and 26'. This added pressure, as the pad 74 conforms to the shape of the human body, ensures that the pad 74 will be held stationary. By stationary, it is meant that the pad 74 will not easily move sideways or lengthwise, forward or rearward relative to the crotch portion of the undergarment 28, any appreciable amount.

Figures 10, 11:
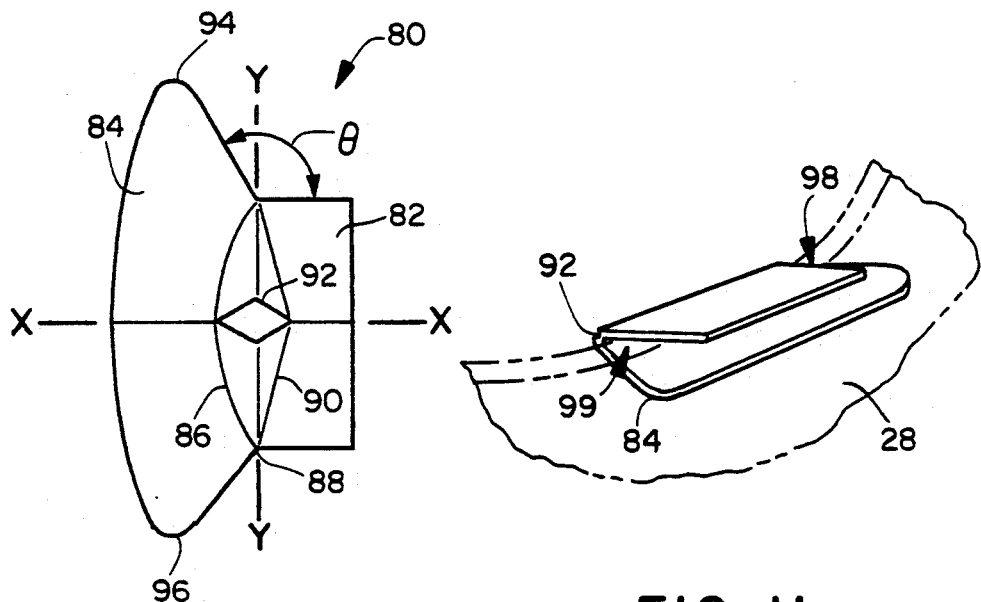
FIG. 10 is a plane view of a clasp having first and second portions joined by three axes of flexibility.
FIG. 11 is a perspective view of a clasp depicted in a closed position and showing the wedge shaped end which traps the undergarment and prevents it from moving lengthwise.

Referring now to FIGS. 10-13, three different embodiments of a clasp are shown. In FIG. 10, a clasp 80 is depicted having a first portion 82 and a second portion 84 joined together and bendable at three different hinge lines 86, 88 and 90. The three hinges or axes of flexibility 86, 88 and 90 allows the clasp 80 to be flexible. The hinges 86, 88 and 90 are arranged such that hinges 86 and 90 are non-linear, that is they are bowed or tapered relative to a transverse centerline x—x and/or to a longitudinal centerline y—y. The non-linear hinges 86 and 90 can be formed by an arcuate line (see hinge 86) or by two intersecting lines having the point of intersection on the transverse axis x—x, (see hinge 90). Preferably, the hinges 86 and 90 are designed such that the second portion 84 can pivot on only one side of a central (horizontal) plane relative to the first portion 82. This configuration assists the wearer of the absorbent article because, as the pad is placed on the undergarment, each of the second portions 84 will be biased toward the closed position wherein each will tightly grasp the undergarment.

A relief 92 is formed along the transverse centerline x—x and is preferably located within the boundary of the outer most hinges 86 and 90. The relief 92 is an opening which divides the hinge 88 into two parts and primarily serves to permit the arcuate shaped portion 84 to pivot relative to the flat first portion 82 without buckling. The clasp 80 further contains two spaced apart ends 94 and 96 which have a smooth or rounded configuration so as not to cause any discomfort to the wearer. The ends 94 and 96 are also angularly configured between the first and second portions 82 and 84, respectively, to form an angle theta ($\theta$) which is greater than 90° and preferably about 145°. The angular configured ends 94 and 96 can be intersected by a line extension of the hinge 88. The angularly configured ends 94 and 96 form approximate V or U-shaped wedges 98 and 99 when the second portion 84 is angularly disposed to the first portion 82, see FIG. 11. The wedges 98 and 99 trap the undergarment 28 and prevent forward and rearward movement of the absorbent article relative to the crotch portion of the undergarment 28.

Figures 12, 13:
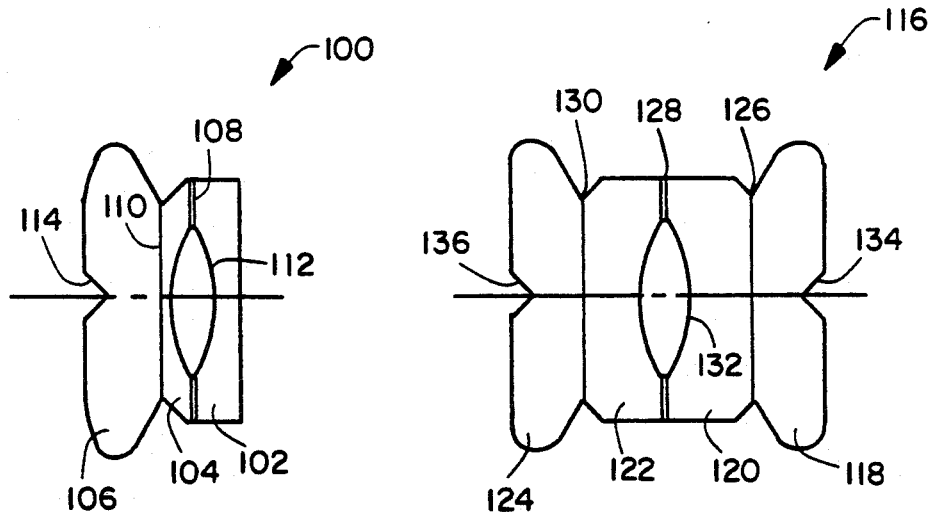
FIG. 12 is a plane view of a second embodiment of a clasp having first and second portions joined by a pair of hinges.
FIG. 13 is a plane view of another embodiment of a clasp having four portions joined by three hinges.

FIG. 12 shows a clasp 100 having first, second and third portions 102, 104 and 106 respectively, wherein adjacent portions are joined together by hinges 108 and 110. A relief 112 is also present between the first and second portions 102 and 104 to provide increased flexibility and divide the hinge 108 into two separate parts. The third portion 106 would be arcuate in shape along the length thereof. A V-shaped notch 114 is cut into the outer exterior edge of the third portion 106 and should be situated along the transverse centerline of the clasp 100. The notch 114 assists in enabling the arcuate portion 106 to flex and bend without buckling.

In FIG. 13, a clasp 116 is shown having four portions designated 118, 120, 122 and 124 wherein the adjacent portions are joined or connected by hinges 126, 128 and 130. The centrally located hinge 128 preferably is formed coaxially with the longitudinal centerline of the pad to which it is affixed. The two outboard hinges 126 and 130 can be "living hinges" and should be situated close to the side edges of the pad. This configuration will enable the pad to conform to the anatomy of the wearer. A relief 132 is formed between the central, relatively flat portions 120 and 122. The outer two portions 118 and 124 are arcuately formed and contain V-shaped notches 134 and 136 to give them added flexibility.

Referring to FIGS. 14 and 15, an undergarment facing surface 138 of an absorbent article 140 is shown having a clasp 142 attached thereto. The clasp 142 contains six portions 144, 145, 146, 147, 148 and 149 connected together by five hinges 150, 151, 152, 153 and 154. Three reliefs 156, 157 and 158 are formed between each pair of portions to give the clasp 142 added flexibility. Each of the two outer hinges 150 and 154 incorporate a pair of elastic members 160 and 162, and 164 and 166, respectively, which tend to be more durable and can bias the arcuate portions 144 and 149 towards their closed positions. The elastic can be made to shrink upon the application of heat and therefore can wrinkle or take on a predetermined set so as to permit the arcuate portions 144 and 149 to flex on only one side of a central plane. For example, in FIG. 15, the elastic 160 allows the arcuate portion 144 to flex only downward relative to the line x—x.

Referring to FIG. 16, a non-slip undergarment facing surface 168 is formed on the lower surface of an absorbent article 170. The non-slip or skid-resistant surface 168 can be formed by using a baffle material having a high coefficient of friction or it can be created by applying a coating to the surface 168. A rubbery type of coating having a thickness of between about 0.1 to 1.0 millimeters, preferably between about 0.5 to 0.8 millimeters, can also be used. By a high coefficient of friction is meant a coefficient of friction around 2.0 or greater. The coefficient of friction of a polyethylene and polypropylene packaging film was tested on a Kayeness Tester with an Omniscribe Recorder. The test method involved placing a sample material on a test table and moving a sled of approximately 200 grams across the surface of the sample. The results indicated that the coefficient of friction was over 2.0 for each sample.

In FIG. 16, four separate and distinct clasps 172, 174, 176 and 178 are formed integrally with the article 170. The clasps are arranged in pairs and each clasp extends outward from the side edges of the article 170. One way to arrange the clasps is to place one pair near the forward end of the absorbent article 170 and position the other pair near the opposite rearward end. It should also be noted that at least one surface, preferably the concave surface, of each of the arcuate portions 172, 174, 176 and 178 can also be skid-resistant. Although this design might be more costly to produce, it would be beneficial for large absorbent articles such as overnight pads.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. An absorbent article comprising:
   a) an absorbent;
   b) a liquid-impermeable baffle attached to said absorbent to form a pad having longitudinally extending sides, distally spaced ends, a body facing surface and a garment facing surface; and
   c) clasp means for holding said pad secure to a garment, said clasp means being more rigid than said pad and including first and second portions joined together by a hinge, said first portion being attached to said baffle and aligned beneath said garment facing surface of said pad, and said second portion having an arcuate shape along the length thereof which functions to squeeze said garment against said pad with increasing force as pressure is applied to said body facing surface of said pad.

2. The absorbent article of claim 1 wherein said clasp means has spaced apart ends and an angular configuration formed at each end between said first and second portions.

3. The absorbent article of claim 1 wherein said first portion of said clasp means is attached to said baffle by an adhesive.

4. The absorbent article of claim 1 wherein said second portion has an arc formed on a radius of between about 5 to 9 inches and is capable of exerting additional pressure on said garment as said second portion is arcuately deformed by pressure impinging on said body facing surface of said pad.

5. The absorbent article of claim 1 wherein said clasp means is stiffer than said absorbent pad.

6. The absorbent article of claim 1 wherein said clasp means is more rigid than said baffle.

7. The absorbent article of claim 1 wherein said clasp means is thicker than said baffle.

8. The absorbent article of claim 1 wherein said clasp means has a thickness ranging from about 0.010–0.125 inches.

9. An absorbent article comprising:
a) a liquid-permeable cover;
b) a liquid-impermeable baffle;
c) an absorbent enclosed by said cover and said baffle to form an absorbent pad, said pad having longitudinally extending sides, distally spaced ends, a body facing surface and a garment facing surface; and
d) clasp means for holding said pad secure to a garment, said clasp means being more rigid than said pad and including first and second portions joined by a hinge, said first portion being attached to said baffle and aligned beneath said garment facing surface of said pad, and said second portion having an arcuate shape along the length thereof which functions to squeeze said garment against said pad with increasing force as pressure is applied to said body facing surface of said pad.

10. The absorbent article of claim 9 wherein said clasp means is a single clasp which extends downward and outward from said baffle when in an open position.

11. The absorbent article of claim 9 wherein said clasp means includes a pair of clasps, each of which extends downward and outward from said baffle when in an open position.

12. The absorbent article of claim 9 wherein said clasp means are attached to said garment facing surface of said pad at points inward of said longitudinal extending sides.

* * * * *

UNITED STATES PATENT AND TRADEMARK OFFICE
CERTIFICATE OF CORRECTION

PATENT NO. : 5,154,715

DATED : October 13, 1992

INVENTOR(S) : Thomas P. Van Iten

It is certified that error appears in the above-identified patent and that said Letters Patent is hereby corrected as shown below:

Column 4, line 19, delete the word "ad" and substitute therefor --and--.

Signed and Sealed this

Twenty-sixth Day of October, 1993

Attest:

BRUCE LEHMAN

*Attesting Officer*    *Commissioner of Patents and Trademarks*